US010463458B2

(12) United States Patent
Jumpertz

(10) Patent No.: US 10,463,458 B2
(45) Date of Patent: Nov. 5, 2019

(54) EXTRAORAL DENTAL SCANNER

(71) Applicant: DENTSPLY SIRONA Inc., York, PA (US)

(72) Inventor: Rainer Jumpertz, Bensheim (DE)

(73) Assignee: DENTSPLY SIRONA Inc., York, PA (US)

( * ) Notice: Subject to any disclaimer, the term of this patent is extended or adjusted under 35 U.S.C. 154(b) by 33 days.

(21) Appl. No.: 14/770,301

(22) PCT Filed: Feb. 27, 2014

(86) PCT No.: PCT/EP2014/053789
§ 371 (c)(1),
(2) Date: Aug. 25, 2015

(87) PCT Pub. No.: WO2014/131816
PCT Pub. Date: Sep. 4, 2014

(65) Prior Publication Data
US 2016/0008111 A1 Jan. 14, 2016

(30) Foreign Application Priority Data
Feb. 27, 2013 (DE) .......................... 10 2013 203 312

(51) Int. Cl.
*A61C 13/34* (2006.01)
*H04N 13/204* (2018.01)
(Continued)

(52) U.S. Cl.
CPC ............ *A61C 13/34* (2013.01); *A61C 9/0093* (2013.01); *G01B 11/24* (2013.01); *H04N 13/204* (2018.05)

(58) Field of Classification Search
CPC ... A61C 13/0004; A61C 9/004; A61C 9/0053; A61C 9/0046; A61C 19/04; A61C 7/146;
(Continued)

(56) References Cited

U.S. PATENT DOCUMENTS 7,335,876 B2 2/2008 Eiff et al.
7,493,182 B2 2/2009 Weber et al.
(Continued)

FOREIGN PATENT DOCUMENTS

DE 43 01 538 A1 7/1994
DE 102 60 670 A1 7/2004
(Continued)

OTHER PUBLICATIONS

English translation of International Search Report dated Jul. 8, 2014, in PCT/EP2014/053789.
(Continued)

*Primary Examiner* — Farhan Mahmud
(74) *Attorney, Agent, or Firm* — Dentsply Sirona Inc.

(57) ABSTRACT

An extraoral dental scanner for three-dimensional capture of the surface of a dental shaped part (300) with a 3D measuring camera (102) having an optical axis (106), wherein the means for the machine-controlled relative positioning of the 3D measuring camera (102) and the dental shaped part (300) are embodied in such a way that the means for taking up and positioning the dental shaped part (300) can be moved into a parking position outside a region that can be captured optically by the 3D measuring camera (102), with a work plate (708) for manually positioning the dental shaped part (300) in the measurement volume (144) of the 3D measuring camera (102), wherein the work plate (708) is aligned perpendicularly to the optical axis (106) and wherein the work plate (708), as viewed from the 3D measuring camera (102), is arranged behind the means for taking up and positioning the dental shaped part (300), makes it possible to record uninterrupted 3D image data with very short recording times both by automatic and by manual positioning of dental shaped parts of different sizes and embodiment variants.

13 Claims, 7 Drawing Sheets

(51) Int. Cl.
*A61C 9/00* (2006.01)
*G01B 11/24* (2006.01)

(58) Field of Classification Search
CPC .......... A61C 7/08; A61C 11/08; A61C 11/02; G01B 11/25; G01B 11/2518; G01B 11/24; G01B 11/2513; G06T 2210/41; G06T 17/00; G06T 2207/30036; G01S 17/89; A61B 6/14; A61B 5/4547
See application file for complete search history.

(56) References Cited

U.S. PATENT DOCUMENTS

| | | | |
|---|---|---|---|
| 7,687,754 B2 | 3/2010 | Eiff et al. | |
| 7,855,354 B2 | 12/2010 | Eiff et al. | |
| 2006/0090361 A1 | 5/2006 | Matsuda et al. | |
| 2007/0046663 A1 | 3/2007 | Brinkmann et al. | |
| 2007/0248929 A1* | 10/2007 | Holzner | A61C 9/00 433/24 |
| 2008/0131833 A1 | 6/2008 | Weber et al. | |
| 2008/0175471 A1 | 7/2008 | Eiff et al. | |
| 2010/0240001 A1 | 9/2010 | Steger | |
| 2011/0090513 A1* | 4/2011 | Seidl | A61C 9/00 356/601 |
| 2013/0025055 A1 | 1/2013 | Saracen et al. | |
| 2014/0168414 A1* | 6/2014 | Brumovsky | G06T 7/0057 348/92 |

FOREIGN PATENT DOCUMENTS

| | | | | |
|---|---|---|---|---|
| DE | 10260670 A1 | 7/2004 | | |
| DE | 20 2005 020 705 U1 | 6/2006 | | |
| DE | 102004054876 B3 | 7/2006 | | |
| DE | 102005016233 A1 | 10/2006 | | |
| DE | 102007030768 A1 | 1/2009 | | |
| EP | 0 600 800 A1 | 6/1994 | | |
| EP | 1 609 437 A | 12/2005 | | |
| EP | 1609437 A1 * | 12/2005 | .......... A61C 9/0093 |
| EP | 2229913 A1 | 9/2010 | | |
| JP | H10-286271 A | 10/1998 | | |
| JP | 2006-006896 A | 1/2006 | | |
| WO | 2008050373 A1 | 5/2008 | | |

OTHER PUBLICATIONS

International Preliminary Report on Patentability (and English translation) dated Sep. 1, 2015, in PCT/EP2014/053789.
Office Action dated Jun. 11, 2013, in German Patent Application No. 10 2013 203 312.5.
International Search Report dated Jul. 8, 2014, in PCT Application No. PCT/EP2014/053789.
English translation of Office Action in Japanese Patent Application No. 2015-558498, dated Oct. 31, 2017.

* cited by examiner

EXTRAORAL DENTAL SCANNER

FIELD OF THE INVENTION

The invention concerns an extraoral dental scanner. With extraoral dental scanners the dental shaped parts to be measured must be positioned during recording in a suitable position in a measurement volume of the scanner. By a dental shaped part is meant dental models such as, for example, maxillary/mandibular models articulated in the articulator, individual full-jaw models, individual single-tooth models, partial jaw models, wax-up models, full-jaw impression trays, counter-bite impression trays. The model is recorded in different views so as to obtain the most complete uninterrupted data possible. Here the surfaces to be scanned should be aligned as perpendicularly as possible to the optical axis of the measurement camera in order to obtain a high quality of data. The measurement volume is a virtual demarcated space which, for example, can have the geometrical shape of an approximate cuboid, within which the relevant areas on the surface of the dental shaped part can be captured three-dimensionally with the optical resources of the scanner.

PRIOR ART

The publication EP 2 229 913 A1 mentions, for example, a device or method for creating three-dimensional images of dental models in which the operator, during the process of digitizing the dental shaped part, can create the most ideal relative positioning possible of the jaw halves or halves of the dental model and capture this by means of the scanner. Preferentially it should also be made possible to capture a realistic solid-angle positioning of the jaw halves relative to each other, thereby extending the possibilities of known structured-light scanners. The device described has a positioning area within which, for example, an articulator with dental model halves inside it can be arranged such that the articulator with the dental model halves can be captured within the scanning field of the scanner at least on an area by area basis. In positioning the dental models it is not a purely virtual positioning of the jaw halves to be scanned which is carried out but rather an ideal manual positioning of the jaw halves relative to each other based on the experience of the operator.

Even in the case of the InEos Blue extraoral scanner, a product of Sirona Dental Systems GmbH, Bensheim, Germany, the dental shaped parts in the optical measurement volume are scanned manually, by shifting and tilting the model on a model holder, as described in DE 10 2004 054 876 A1 or DE 10 2007 030768 A1. Even to focus the measurement camera it must be moved manually parallel to its optical axis, possibly before every recording. Since the image field is relatively small here as well, a very large number of individual recordings must be made especially to record a complete jaw model. A very great deal of interaction with the device is therefore necessary. Only the recording of individual tooth stumps has, as regards rotation, motorized support by means of a rotation mouse.

PROBLEM

The purpose of the invention is to provide an improved extraoral dental scanner.

SOLUTION

This problem is solved by the invention with the features of the independent claim. Advantageous developments of the invention are indicated in the subordinate claims. The wording of all claims is hereby incorporated into the content of the present description by reference.

As solution to the problem an extraoral dental scanner for the three-dimensional capture of the surface of a dental shaped part is proposed,
- having a 3D measuring camera for the three-dimensional capture of the surface of the dental shaped part in a measurement volume of the 3D measurement camera, the 3D measurement camera having an optical axis;
- having means for holding and positioning the dental shaped part, and
- having means for the machine-controlled positioning of the 3D measurement camera and of the dental shaped part
- the means for the machine-controlled relative positioning of the 3D measurement camera and of the dental shaped part being designed such that the means for holding and positioning the dental shaped part can be moved into a parking position outside the region which can be optically captured by the 3D measurement camera;
- [having] a work plate for the manual positioning of the dental shaped part in the measurement volume of the 3D measurement camera, the work plate being aligned perpendicularly to the optical axis and the work plate as seen from the 3D measurement camera being arranged behind the means for holding and positioning the dental shaped part.

The automatic positioning of the dental shaped part and the processing of the 3D images of the surfaces of the dental shaped part captured by the scanner are carried out under machine or computer control.

The work plate for the manual positioning of the dental shaped part in the measurement volume of the 3D measurement camera is as seen from the 3D measurement camera arranged behind the means for holding and positioning the dental shaped part. Here the work plate typically lies in a plane perpendicular to the first optical axis.

The means for the machine-controlled relative positioning of the 3D measurement camera and of the dental shaped part are designed in such a way that the means for holding and positioning the dental shaped part can be moved into a parking position outside a region which can be captured optically by the 3D measurement camera so that it is possible to examine models on the work plate without shading the measurement lens and to create a maximum of free space. This is especially important for manual mode. In this way the model rotation module with the model plate is parked outside an image field to be captured by the 3D measurement camera and manual positioning of the dental shaped part is not hindered.

To implement the option of an automatic or a manual positioning of the model (hybrid model positioning) the extraoral dental scanner has two work areas, namely a work area for automatic model positioning and a work area (working plane) for manual model positioning, the work plate being arranged in the working plane for manual model positioning.

Manual positioning has the advantage of rapid intuitive positioning of the object within the measurement volume, for example when only a few individual recordings are required, and also with dental shaped parts which cannot be moved by the automatic positioning means on account of their size. With the manual positioning mode any dental shaped parts can be positioned by hand on the work plate up to and including models which are articulated in large articulators, for example, for direct buccal insertion. For this purpose suitable model holders or trays are used in practice. This mode offers additional advantages, such as when the relevant recording area is small and only a few recordings are required to capture it completely.

Automatic or machine-controlled positioning generally offers the advantage that image sequences up to and including full jaw geometries can be recorded without interaction. Here in the case of the usual types of model all relevant surfaces are scanned in such a way as to produce uninterrupted data.

In automatic or machine-controlled positioning mode nearly all major dental shaped parts commonly found in dental laboratories can be recorded by an operator without interaction (but not models in large articulators).

In this development the extraoral dental scanner makes it possible to record uninterrupted 3D image data with very short recording times not only by the automatic but also by the manual positioning of dental shaped parts of different sizes and design variants.

The means for the machine-controlled relative positioning of the 3D measurement camera and of the dental shaped part can advantageously include the following elements:
 a first camera elevation module for moving the 3D measurement camera along a first linear axis;
 a second tilting module with a second rotational axis;
 a third swiveling module with a third rotational axis;
 a fourth model-height compensation elevation module with a fourth linear axis;
 a fifth model rotation module with a fifth rotational axis; and
 a model plate to hold the dental shaped part.

Here the second tilting module is rotationally fixed to one side of the first camera elevation module, in the same way as the third swiveling module is rotationally fixed to one side of the second tilting module. The fourth model-height compensation elevation module is movably fixed to the third swiveling module. The model rotation module is attached to the model-height compensation elevation module in such a way that the fifth rotational axis of the model rotation module runs parallel to the fourth linear axis. The model plate is supported rotationally on the model rotation module, the center of the model plate lying on the fifth axis of rotation. The first linear axis, the second axis of rotation and the third axis of rotation in each case are perpendicular to each other and intersect at the central point of the measurement volume.

The proposed five-axis system offers all of the degrees of freedom required to view all areas of a dental shaped part.

The optomechanical positioning system used in the proposed extraoral dental scanner is a very freely movable special 5-axis positioning system for positioning the measurement volume of the 3D measurement camera relative to a dental shaped part. Here the freedom of movement and the size and also the position of the measurement volume relative to the positioning system are so harmonized to each other that the relevant model geometries of dental shaped parts can be recorded almost completely from favorable viewing angles, namely as perpendicularly as possible to the surfaces. Special axial parameter combinations make it possible to capture model geometries completely and systematically in specific recording modes.

Due to the design of the extraoral dental scanner the model can be moved so freely that all areas of the model can be viewed and the optical axis of the recording system here stands as perpendicularly as possible to the surfaces to be recorded. The automatic positioning system compensates for different model heights in such a way that clamping can be carried out by the operator without subsequent adjustment.

In all recording modes different model heights are automatically compensated by the separate linear drive module as model-height compensation elevation module.

When the fifth axis of rotation is at a distance from the first linear axis, when the second and third axes of rotation are set such that the fifth axis of rotation is parallel to the first linear axis, this makes it possible to make a complete recording of, for example, a full set of teeth by simply rotating the model plate.

The means for the relative positioning of the 3D measurement camera and of the dental shaped part can advantageously have the following angular and/or travel ranges with respect to a neutral position, namely:
 a) the first linear axis of the first camera elevation module for moving the 3D measurement camera along the first linear axis over a travel range of plus 25 mm to minus 170 mm;
 b) the second axis of rotation of the second tilting module over an angular range of plus 60° to minus 60°;
 c) the third axis of rotation of the third tilting module over an angular range of plus 60° to minus 105°;
 d) the fourth linear axis of the fourth model-height compensation elevation module over a travel range of plus 25 mm to minus 25 mm; and
 e) the fifth axis of rotation of the fifth model rotation module over an angular range of 360° and/or multiples thereof.

The second and third axes of rotation together form a unilateral gimbal mount. This cardan joint makes it possible to tilt the model in each case freely by +/−60° with respect to the 3D measurement camera.

If a point on the surface of the dental shaped part is located at the intersection of axis 2 and axis 3, it can then be wobbled by means of the angular ranges of the second and third axes of rotation. In this way it can be measured very rapidly by the 3D measurement camera without wandering out of the focal plane and without it being necessary to readjust the other axes.

This wobbling (wobble scanning mode) does not cause the relevant point on the surface of the dental shaped part to move away from the intersection of the second and third axes of rotation. Here the surface of the shaped part at this point changes its spatial orientation but not the spatial location of the point. In this way, in wobble scanning mode, when, for example, several individual tooth stumps are arranged on the model plate, it is possible to scan them successively in one clamping operation, as in the case of a single-tooth rotation scan, without the individual tooth models needing to be clamped separately. The center point of the cardan joint (intersection of the second and third axes of rotation) is located in wobble scanning mode at the center of the measurement volume, which means that the model does not wander out of the measurement volume when being tilted.

One of the two cardan axes of rotation, namely the third axis of rotation, can be swiveled in one direction up to 105°, which in rotation scanning mode has allowed a view into geometries with undercuts relative to the 3D measurement camera and which could not be captured by tilting only up to 60°.

It is advantageous when the extraoral dental scanner is designed in such a way that the model plate is circular and thus has a radius. Here the fifth axis of rotation of the model rotation module runs through the center of the model plate and the diagonal of the image field of the 3D measurement camera is at least as long as the radius of the model plate. In this way a full capture and measurement of an object arranged on the model plate is obtained.

In rotation scanning mode with the aid of the model plate, e.g. complete jaw models can be recorded not only buccally but also lingually by rotating the fifth axis of rotation supplementarily to an overview recording, which usually results in a high overall data density.

By means of a synchronous activation of the camera elevation module with the first linear axis, of the tilting module with the second axis of rotation and the model rotation module with the fifth axis of rotation, laterally protruding models wider than the image field can be moved laterally with respect to the camera during the rotation scan and thus be fully captured. Here the axis of the model-height compensation module (fourth axis) can be used as a feed axis. In this way, models longer than the image field diagonal, among other things, can be recorded, for example, wax-up models and triple trays. Should they protrude laterally from the image field during rotation, this can be compensated by synchronous movement of the second and fifth axes.

It is advantageous when in the extraoral dental scanner the distance of the fifth axis of rotation from the first linear axis is at least 22 mm but no more than 26 mm, and preferably 24 mm, when the second and third axes of rotation are set such that the fifth axis of rotation runs parallel to the first linear axis. This results in an offset of the rotational axis center of the fifth axis of rotation to the cardan joint center (intersection of the second and third axes of rotation) when the robot arm is in the neutral position.

This allows the use of a camera with a relatively small image field. The image field of the camera can be aligned such that it in its diagonal extends from the center of the model plate to the edge of the model plate. A complete recording of, for example, a full set of teeth can be obtained by joining together several recordings with a step-by-step rotation of the model plate.

A camera with a relatively small image field and fixed focus is not at all expensive. This means that the proposed extraoral dental scanner can be manufactured considerably more cheaply than previously possible.

For optical capture of the surface of the dental shaped part the 3D measurement camera of the dental shaped part can have an optical image-recording camera and a structured-light projector. The three-dimensional capture of the surface of the dental shaped part will then be based on the principle of a planar triangulation which has proved very satisfactory in the dental field. Alternatively, different 3D measurement methods could also be used, such as, for example, stereoscopic recording techniques.

By triangulation is meant a geometrical method of optical distance measurement by precise angular measurement in triangles. When the beam direction and the distance between a camera and a light source are known the distance between the camera and points on the surface of an object can be determined. The connection between camera and light source and also the two beams from and to the object here form a triangle, whence the term triangulation is obtained. With this method it is possible to obtain a three-dimensional capture, in other words, measurement of the entire surface of an object, which is termed planar triangulation.

By means of the camera elevation module (linear drive module) along the first linear axis the camera can be focused with the aid of an autofocus controller before every recording and without manual intervention. Here it is advisable with the extraoral dental scanner to connect the camera elevation module to an image-processing device for automatic focusing of the 3D measurement camera. In the 3D measurement camera, autofocusing is not implemented by altering interlens separations inside the camera lens system but by linear movement of the 3D measurement camera along the first linear axis by means of a linear drive module.

This means that a particularly inexpensive fixed-focus camera can be used. A camera of this kind can deliver a very high image resolution at low cost.

In the case of manual positioning of the dental shaped part it is advantageous for the proposed extraoral dental scanner to have at least one photoelectric beam for rough positioning of the 3D measurement camera. This is followed by fine positioning by means of the autofocus device.

The special combination implemented in the proposed extraoral dental scanner of the smallest possible measurement volume (which means higher measurement precision at a similar cost for the optics) relative to the relevant model sizes and an axis arrangement and axis travel paths for almost any relative movement of the measurement volume with respect to the model makes it possible to scan almost all relevant model geometries not only manually but also automatically in one and the same device optically almost completely from favorable viewing directions.

With its optomechanical positioning axis concept the proposed extraoral dental scanner makes possible even more as yet unmentioned special recording modes.

In an overview recording mode, whole jaw models and whole jaw impression trays, for example, can, after adjustment for the model height by the fourth axis, be essentially almost completely captured by rotation of the fifth axis in, for example, five equally large angular steps.

In an additional recording mode localized data gaps can be filled via special recording planning by calculating as viewing direction an axial coordinates combination which is ideal for the gap in question. Here the high freedom of movement of the axial system is fully exploited, which results in almost gapless data sets.

Further details and features arise from the following description of a preferred embodiment in conjunction with the subordinate claims. Here the features in question can be realized on their own or combined together in groups. The possibilities of solving the problem are not limited to the example. For example, range figures, for example, always cover all—not explicitly stated—intermediate values and all conceivable sub-intervals.

BRIEF DESCRIPTION OF THE DRAWING

The example embodiment is presented schematically in the drawings. The same reference numbers in the individual drawings here refer to the same elements or to functionally equivalent elements or to mutually corresponding elements as regards their functions. In detail.

EMBODIMENT OF THE INVENTION

Figure 1:
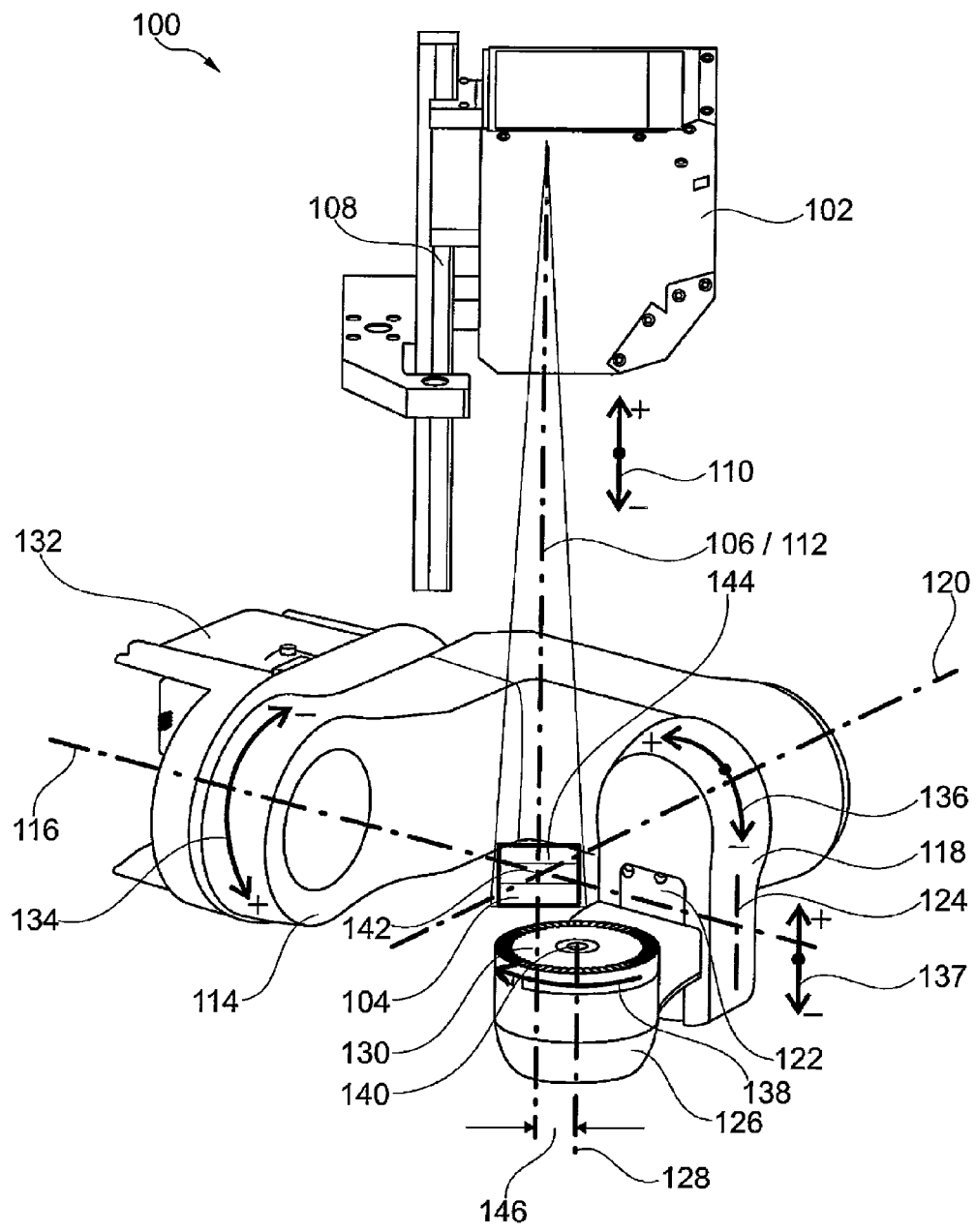
FIG. 1 shows a partial view (schematic) of the extraoral dental scanner with its main parts (without housing) and a representation of the position of the measurement volume in relation to the positioning axes.

The extraoral dental scanner 100 shown schematically in its neutral position in the partial view in FIG. 1 and used for the three-dimensional capture of the surface of a dental shaped part has the following principal elements or assemblies which are arranged inside a housing (not shown):

- a 3D measuring camera 102 for the three-dimensional capture of the surface of the dental shaped part in a measurement volume 104 of the 3D measurement camera 102, the 3D measurement camera 102 having an optical axis 106 and a measurement volume 104;
- means for the relative positioning of the 3D measurement camera 102 and of the dental shaped part, namely:
- a camera elevation module (linear drive module) 108 for the vertical movement of the 3D measurement camera 102 in either direction 110 along a linear axis 112 (first axis), whose position is identical to that of the optical axis 106 of the 3D measurement camera 102;
- a tilting module 114 with an axis of rotation 116 (second axis);
- a swiveling module 118 with an axis of rotation 120 (third axis);
- a model-height compensation elevation module 122 with a linear axis 124 (fourth axis);
- a model rotation module 126 with an axis of rotation 128 (fifth axis); and
- a model plate 130 to hold the dental shaped part.

The measurement volume is defined by the image field of the camera (x,y), here typically 30 mm×40 mm, with a depth corresponding to the depth of field of the camera, here typically ±10 mm above and below a focus plane.

The camera elevation module (linear drive module) 108 takes the form of an immovable assembly on which the 3D measurement camera is arranged.

Beneath the camera elevation module 108 a further immovable assembly 132 is arranged to which the tilting module 114 is attached on one side and rotatably in two directions 134. The tilting module 114 takes the form of a right angle with two legs.

The swiveling module 118 is attached to the further leg of the tilting module 114 on one side and rotatably in two directions 136.

The combination of tilting module 114 and swiveling module 118 has a similar design to a robot arm and forms a cardan joint or cardan arm.

The model-height compensation elevation module 122 is attached to the swiveling module 118 so that it can be moved linearly in two directions 137.

The model rotation module 126 is here attached to the model-height compensation elevation module 122 in such a way for a rotation in a given direction 138 that the axis of rotation 128 of the model rotation module 126 runs parallel to the linear axis 124 of the model-height compensation elevation module 122. The model plate 130 for holding the dental shaped part is rotatably mounted with a predetermined direction 138 on the model rotation module 126, whereby the center 140 of the model plate 130 lies on the axis of rotation 128 of the model rotation module 126.

The linear axis 112 of the camera elevation module 108 (and thus the optical axis 106 as well), the axis of rotation 116 of the tilting module 114 and the axis of rotation 120 of the swiveling module 118 stand in each case perpendicular to each other and intersect at the center 142 of the measurement volume 144.

The axis of rotation 128 of the model rotation module 126 is separated from the optical axis of the 3D measurement camera by a distance 146 when the axis of rotation 116 of the tilting module 114 and the axis of rotation 120 of the swiveling module 118 are adjusted so that the axis of rotation 128 of the model rotation module 126 is aligned parallel to the optical axis 106 of the 3D measurement camera 102.

The 3D measurement camera 102 has both an optical camera and a structured-light projector (neither illustrated separately).

A structured-light projector or structured-light projection is a device or method of contactlessly capturing the three-dimensional shape of a surface of an object. On the triangulation principle stripes are projected onto the object under investigation and detected by a camera at a defined angle. The lateral deflection of the stripes detected by the camera is here a measure of the height of the object or individual points on a surface of the object.

In automatic positioning mode the linear drive module (camera elevation module) 108 moves the 3D measurement camera 108 and thus the measurement volume 144 with the aid of an autofocus controller before every recording and without any manual interaction along the linear axis 112 parallel to the optical axis 106 of the camera into the area of the dental shaped part which is to be recorded.

The means shown in FIG. 1 for the relative positioning of the dental shaped part (tilting module 114, swiveling module 118, model-height compensation elevation module 122, model rotation module 126 with the model plate 130) can be moved or rotated within specific ranges. In Table 1 below the angular or travel ranges with respect to the neutral position shown in FIG. 1 are listed:

TABLE 1

| Reference number | Designation of axis | Neutral position | Max. range |
|---|---|---|---|
| 112 | First linear axis | 0 mm | +25/−170 mm |
| 116 | Second axis of rotation | 0° | +60°/−60° |
| 120 | Third axis of rotation | 0° | +60°/−105° |
| 124 | Fourth linear axis | 0 mm | +25/−25 mm |
| 128 | Fifth axis of rotation | 0° | n × 360° |

The directions of the signing convention are marked beside the corresponding axes in FIG. 1.

Figure 2:
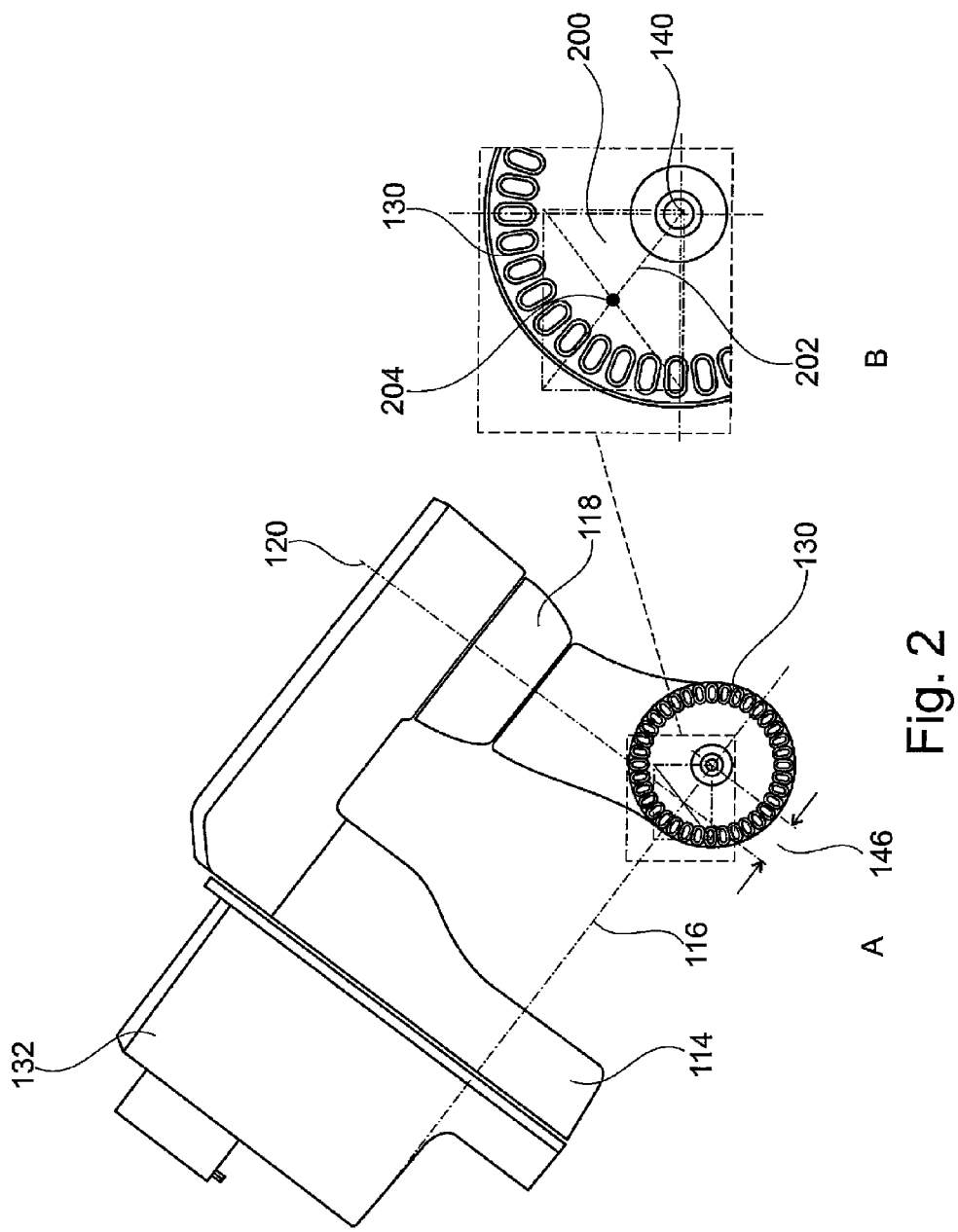
FIG. 2A shows a second partial view (schematic) of the parts of the extraoral dental scanner with a representation of the position of the measurement volume in relation to the positioning axes.
FIG. 2B shows a magnified section of FIG. 2A in the region of the measurement volume.

In FIG. 2 by means of a partial view (View A) of the immovable assembly 132 beneath the camera elevation module 108 and the positioning means 114, 118, 126, 130, 114 the position of the measurement volume 144 or image field 200 is indicated.

The size of the image field 200 (width×height) here measures 40 mm×30 mm. The resulting length of the image field diagonal 202 is therefore 50 mm. The image field diagonal 202 here more than covers the radius of the model plate 130. The image field center 204 is identical to the intersection point 142 of the cardan axes 116, 120.

The offset (distance) 146 between the model rotation axis 128 of the circular model plate 130 on the one side and the intersection 142 of the axis of rotation 120 of the swiveling module 118 with the axis of rotation 116 of the tilting module 114, in other words, at the center 142 of the cardan joint in the neutral position of the robot arm, measures 24 mm.

View B in FIG. 2 shows a magnified section of View A in order to show the position and size of the image field 200 relative to the model rotation plate 130. The description of View A here applies analogously.

Figure 3:
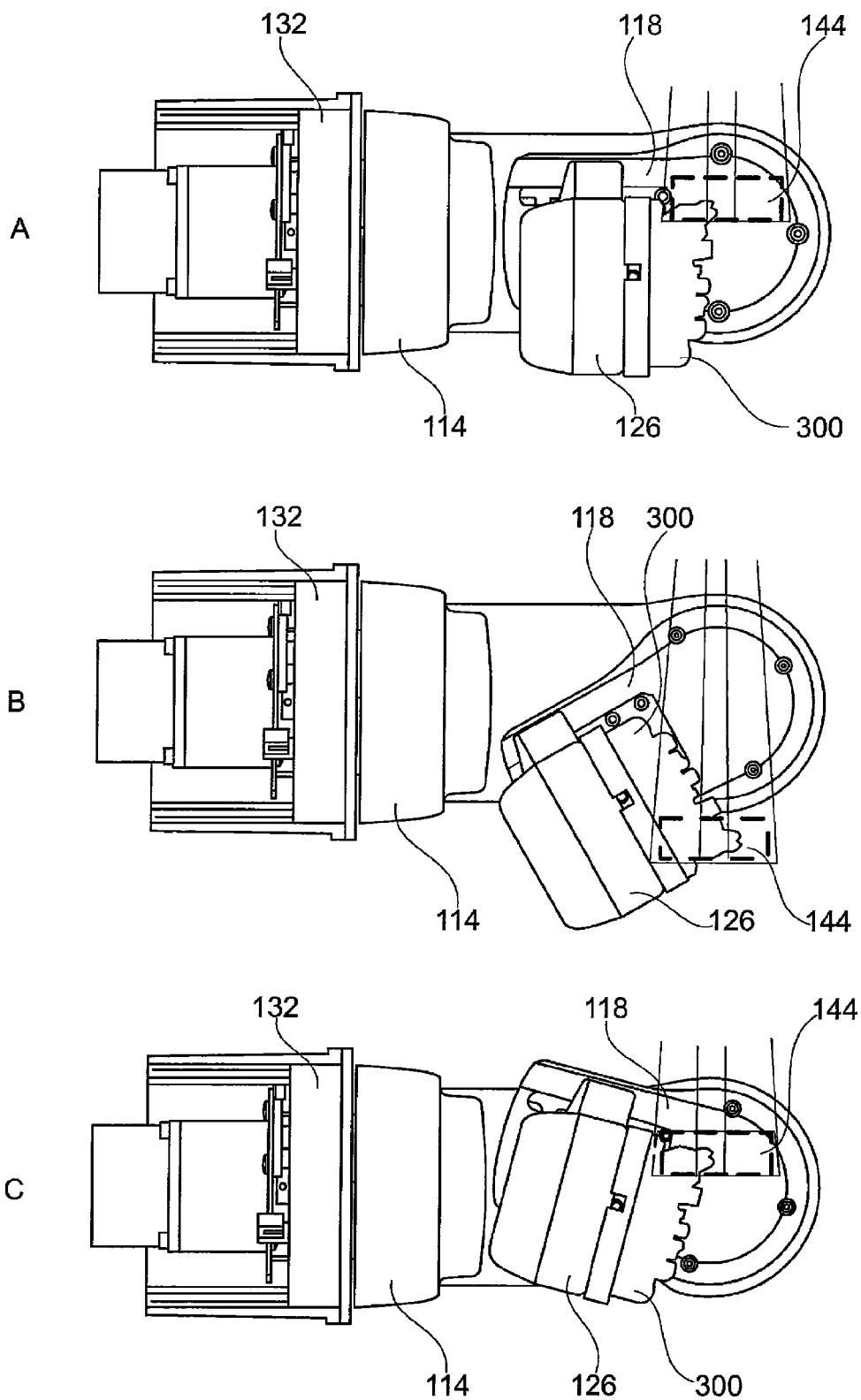
FIG. 3A shows a partial view (schematic) of the extraoral dental scanner with a representation of the position of the measurement volume in the example of a rotation scan (buccal) of a full jaw model.
FIG. 3B shows a partial view (schematic) of the extraoral dental scanner with a representation of the position of the measurement volume in the example of a rotation scan (lingual) of a full jaw model.
FIG. 3C shows a partial view (schematic) of the extraoral dental scanner with a representation of the position of the measurement volume in the example of a measurement involving undercuts.

In FIG. 3 in three partial views (Views A, B and C; schematic) of the extraoral dental scanner 100 in each case a position and angle-related orientation of the positioning means 108, 114, 118, 126, 130 or of the dental shaped part 300 during performance of a rotation scan (buccal and lingual) of a dental shaped part 300 embodied as a full jaw model is demonstrated.

The dental shaped part 300 is arranged on the model plate 130 by means of, for example, a magnetic holder (not illustrated). In this mode the tilting module 114 is in the neutral position (angle of rotation of the second axis of rotation 116 equal to 0°). The relative positioning of the dental shaped part 300 for the three-dimensional capture of its surface is carried out in this mode by varying the coordinates at the first linear axis 112 for moving the camera elevation module 108, at the axis of rotation 120 of the swiveling module 118, at the linear axis 124 for moving the model-height compensation elevation module 122 and at the axis of rotation 128 of the model rotation module 126. The surface of the dental shaped part 300 is here captured from both the buccal and the lingual direction.

The relative positions or rotation angles shown by way of example in FIG. 3 at axes 112, 116, 120, 124, 128 of the positioning means 112, 116, 120, 124, 128 relative to the measurement volume 144 of the 3D measurement camera 102 are given below in the Tables 2 to 4 corresponding to Views A, B and C.

TABLE 2

(View A)

| Reference number | Designation of axis | Coordinate |
|---|---|---|
| 112 | First linear axis | +10 mm |
| 116 | Second axis of rotation | 0° |
| 120 | Third axis of rotation | −90° |
| 124 | Fourth linear axis | +10 mm |
| 128 | Fifth axis of rotation | 8 × 45° |

TABLE 3

(View B)

| Reference number | Designation of axis | Coordinate |
|---|---|---|
| 112 | First linear axis | −62 mm |
| 116 | Second axis of rotation | 0° |
| 120 | Third axis of rotation | −60° |
| 124 | Fourth linear axis | −18 mm |
| 128 | Fifth axis of rotation | 8 × 45° |

TABLE 4

(View C)

| Reference number | Designation of axis | Coordinate |
|---|---|---|
| 112 | First linear axis | +10 mm |
| 116 | Second axis of rotation | 0° |
| 120 | Third axis of rotation | −105° |
| 124 | Fourth linear axis | +10 mm |
| 128 | Fifth axis of rotation | 8 × 45° |

Figure 4:
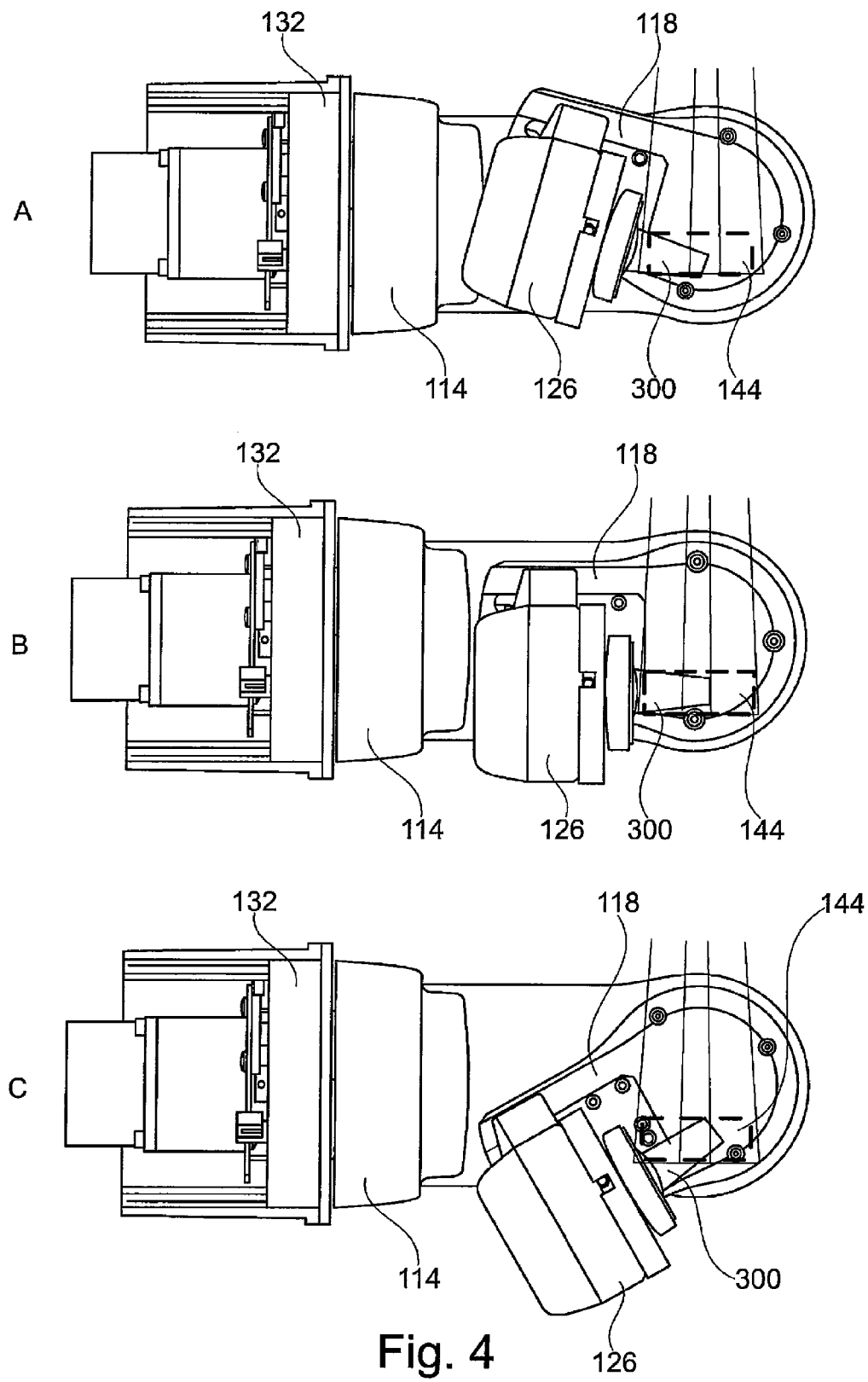
FIG. 4A shows a partial view (schematic) of the extraoral dental scanner with a representation of the position of the measurement volume in the example of a measurement involving undercuts in an individual tooth model in the rotation scan.
FIG. 4B shows a partial view (schematic) of the extraoral dental scanner with a representation of the position of the measurement volume in the example of a rotation scan of an individual tooth model.
FIG. 4C shows a partial view (schematic) of the extraoral dental scanner with a representation of the position of the measurement volume in the example of a rotation scan of an individual tooth model from a different viewing angle.

In FIG. 4 in three partial views (Views A, B and C; schematic) of the extraoral dental scanner 100 a position and angle-related orientation of the positioning means 108, 114, 118, 126, 130 or of the dental shaped part 300 is also demonstrated, but here during performance of a rotation scan of a dental shaped part 300 embodied as an individual tooth model.

The dental shaped part 300 is arranged on the model plate 130 by means of a holder (not illustrated). In this mode the tilting module 114 is also in the neutral position (angle of rotation of axis 2 equal to 0°). The relative positioning of the dental shaped part 300 for the three-dimensional capture of its surface is carried out in this mode analogously to FIG. 3 but here by varying the coordinates at axes 112, 120, 124, 128.

The relative positions or rotation angles 112, 116, 120, 124, 128 shown by way of example in FIG. 4 at the axes of the positioning means 108, 114, 118, 126, 130 are given below in the Tables 5 to 7 corresponding to Views A, B and C.

TABLE 5

(View A)

| Reference number | Designation of axis | Coordinate |
|---|---|---|
| 112 | First linear axis | −20 mm |
| 116 | Second axis of rotation | 0° |
| 120 | Third axis of rotation | −105° |
| 124 | Fourth linear axis | −10 mm |
| 128 | Fifth axis of rotation | 8 × 45° |

TABLE 6

(View B)

| Reference number | Designation of axis | Coordinate |
|---|---|---|
| 112 | First linear axis | −20 mm |
| 116 | Second axis of rotation | 0° |
| 120 | Third axis of rotation | −90° |
| 124 | Fourth linear axis | −10 mm |
| 128 | Fifth axis of rotation | 8 × 45° |

TABLE 7

(View C)

| Reference number | Designation of axis | Coordinate |
|---|---|---|
| 112 | First linear axis | −25 mm |
| 116 | Second axis of rotation | 0° |
| 120 | Third axis of rotation | −60° |
| 124 | Fourth linear axis | −18 mm |
| 128 | Fifth axis of rotation | 8 × 45° |

Figure 5:
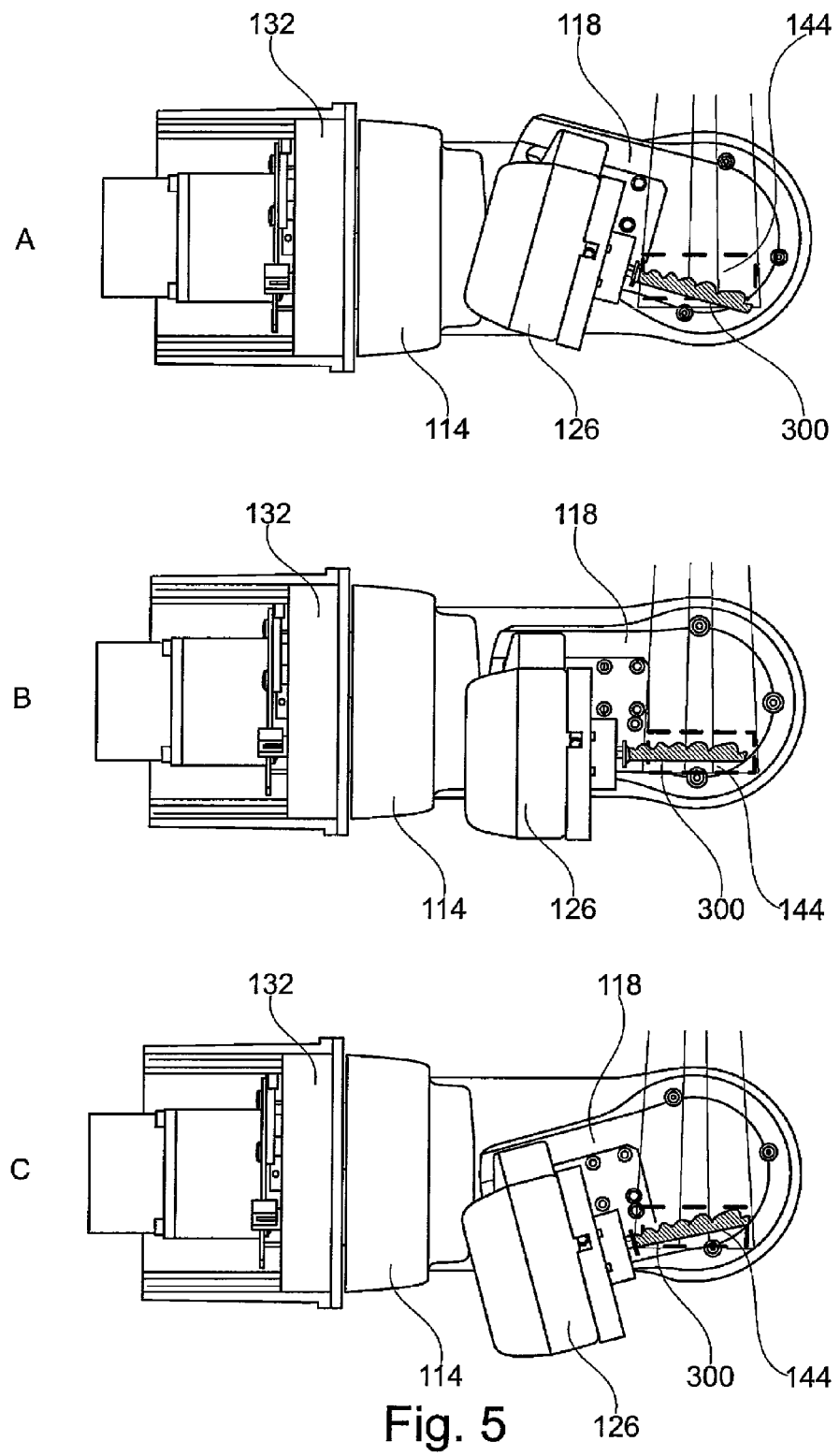
FIG. 5A shows a partial view (schematic) of the extraoral dental scanner with a representation of the position of the measurement volume in the example of a measurement involving undercuts in a dental bridge model.
FIG. 5B shows a partial view (schematic) of the extraoral dental scanner with a representation of the position of the measurement volume in the example of a rotation scan of a dental bridge model.
FIG. 5C shows a partial view (schematic) of the extraoral dental scanner with a representation of the position of the measurement volume in the example of a rotation scan of a dental bridge model from a different viewing angle.
Figure 6:
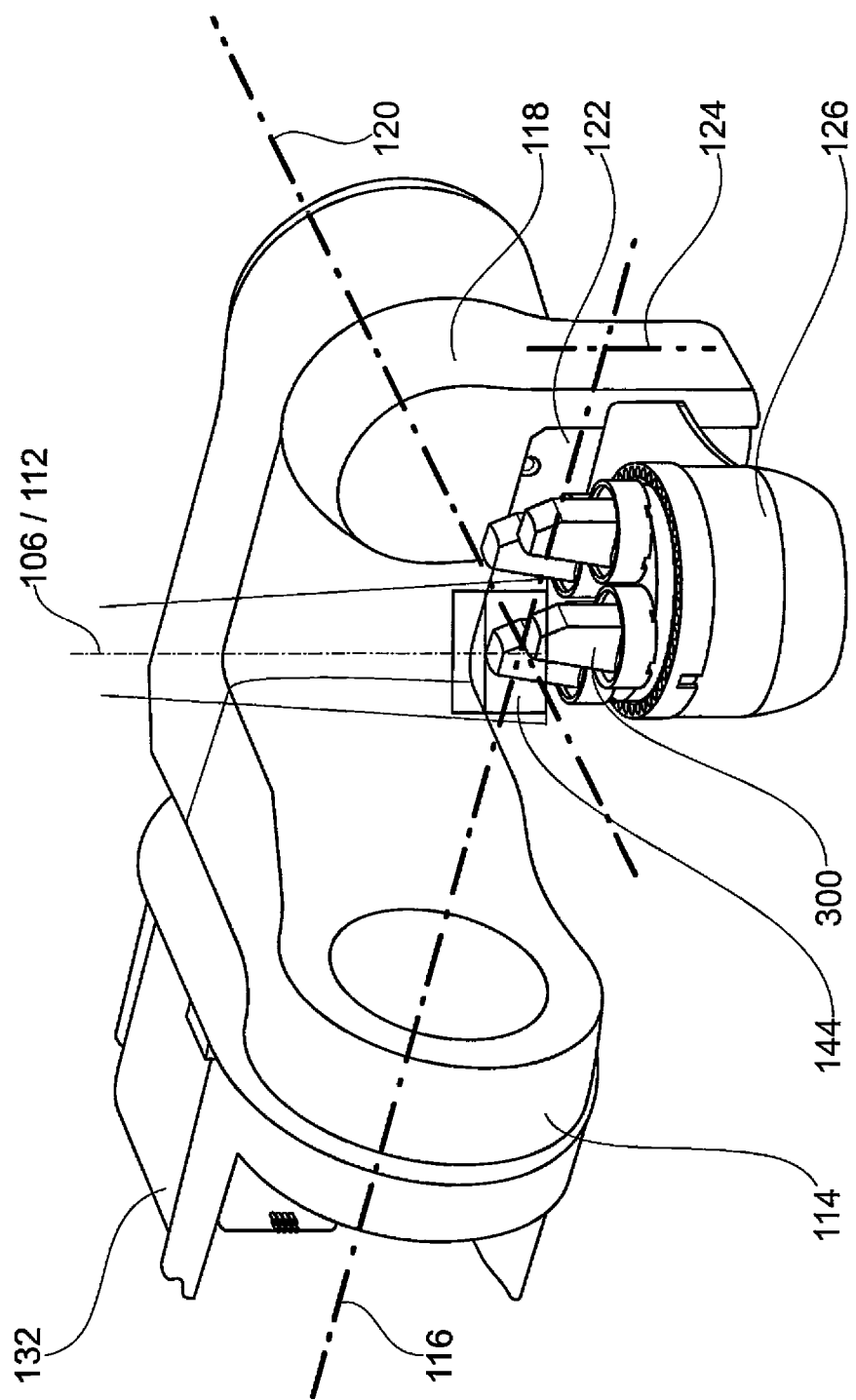
FIG. 6 shows a partial view (schematic) of the extraoral dental scanner in wobble scanning mode in the example of a multiple individual-tooth wobble scan.

In FIG. 5 in three further partial views (Views A, B and C; schematic) of the extraoral dental scanner 100 a position and angle-related orientation of the positioning means 108, 114, 118, 122, 126 or of the dental shaped part 306 is also demonstrated, here during performance of a rotation scan of a dental shaped part 300 embodied as a dental bridge model.

The dental shaped part 300 is arranged on the model plate by means of a holder (not illustrated). In this mode the tilting module 114 is also in the neutral position (angle of rotation of axis 116 equal to 0°). The relative positioning of the dental shaped part 300 for the three-dimensional capture of its surface is carried out in this mode as well analogously to FIGS. 3 and 4, here again by varying the coordinates at axes 112, 120, 124, 128.

The relative positions or rotation angles shown by way of example in FIG. 5 at the axes of the positioning means 108, 114, 118, 122, 126 are given below in Tables 8 to 10 corresponding to Views A, B and C.

TABLE 8

(View A)

| Reference number | Designation of axis | Coordinate |
|---|---|---|
| 112 | First linear axis | −20 mm |
| 116 | Second axis of rotation | 0° |
| 120 | Third axis of rotation | −105° |
| 124 | Fourth linear axis | −10 mm |
| 128 | Fifth axis of rotation | 8 × 45° |

TABLE 9

(View B)

| Reference number | Designation of axis | Coordinate |
|---|---|---|
| 112 | First linear axis | −25 mm |
| 116 | Second axis of rotation | 0° |
| 120 | Third axis of rotation | −90° |
| 124 | Fourth linear axis | −18 mm |
| 128 | Fifth axis of rotation | 8 × 45° |

TABLE 10

(View C)

| Reference number | Designation of axis | Coordinate |
|---|---|---|
| 112 | First linear axis | −25 mm |
| 116 | Second axis of rotation | 0° |
| 120 | Third axis of rotation | −75° |
| 124 | Fourth linear axis | −18 mm |
| 128 | Fifth axis of rotation | 8 × 45° |

FIG. 5 shows a schematic partial view of the immovable assembly 132 and also the arrangement of tilting module 114, swiveling module 118, model-height compensation elevation module 122 and model rotation module 126 during performance of a multiple individual-tooth scan. The dental shaped parts 300 embodied as individual tooth models (here, for example, four individual tooth models) are here arranged on the model plate 130 by means of holders. With this so-called 'wobble scanning mode' it is possible by varying the angles of the second and third axes of rotation 116, 120 to effect a change in the spatial orientation of each of the dental shaped parts 300 at a specific point on the surface without changing the spatial location of this point. In this way the individual tooth model 300 to be scanned remains at all times inside the measurement volume during wobble scanning mode. In this way, for each of the individual tooth models 300 arranged on the model plate 130 the surface can successively be fully captured from different directions by the scanner 100.

In the case of wobble scanning mode the following angles of the second tilting module 114 and of the third swiveling module 118 are for example taken up successively:

TABLE 11

| Angle of the second tilting module 114 | Angle of the third swiveling module 118 |
|---|---|
| −60° | −60° |
| 0° | −60° |
| +60° | −60° |
| +60° | 0° |
| +60° | +60° |
| 0° | +60° |
| −60° | +60° |
| −60° | 0° |

A recording in which both the second tilting module 114 and also the third swiveling module 118 are set to 0° corresponds to a recording from above.

Figure 7:
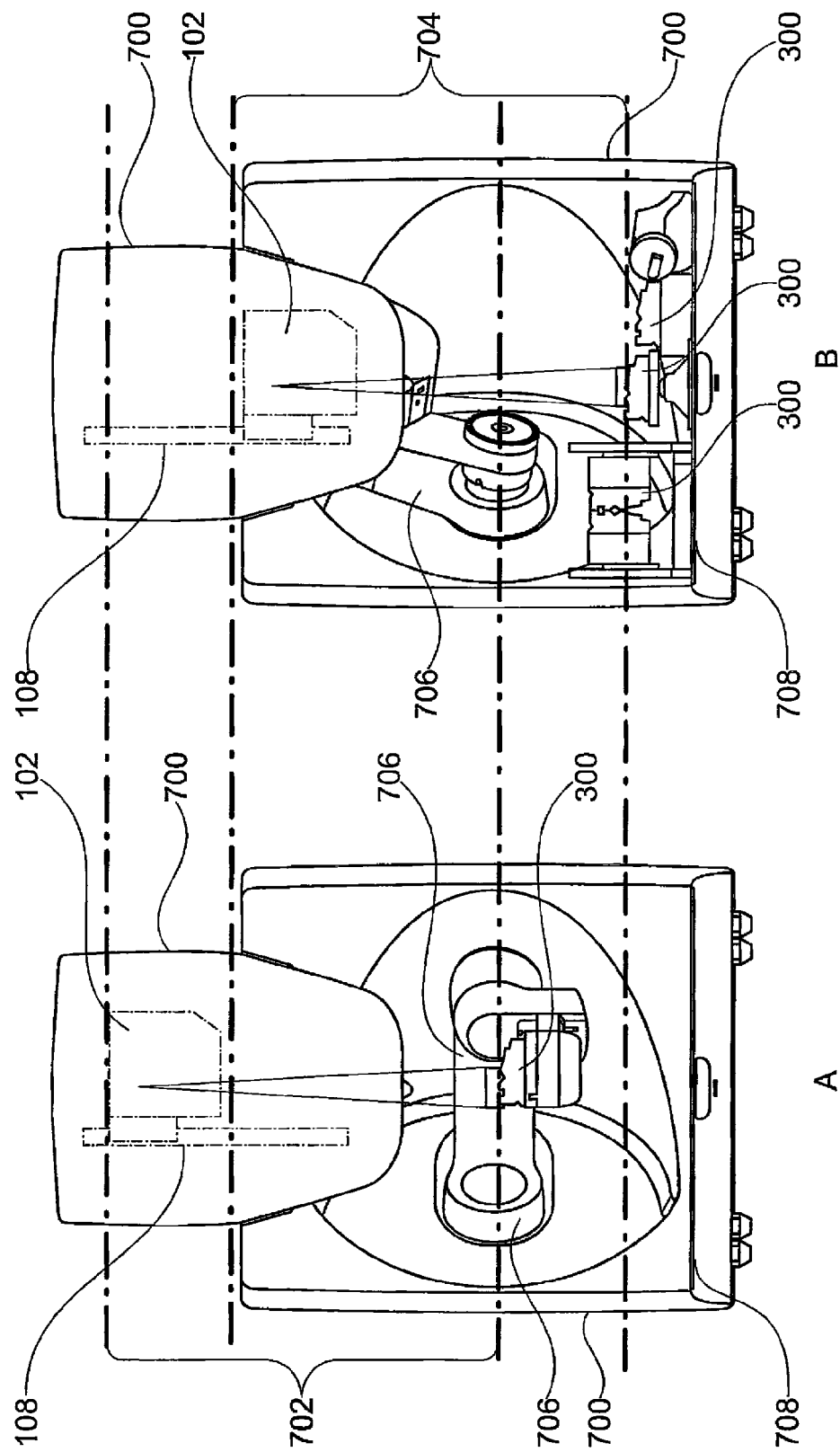
FIG. 7A shows a view (schematic) of the extraoral dental scanner in automatic positioning mode.
FIG. 7B shows a view (schematic) of the extraoral dental scanner in manual positioning mode.

FIG. 7 shows the extraoral dental scanner 100 with the assemblies/elements already described in FIG. 1 arranged in the housing 700 in automatic positioning mode (View A) and in manual positioning mode (View B).

To implement both automatic and manual positioning modes the extraoral dental scanner 100 has in addition to the elements or assemblies already designated in FIG. 1 two vertically arranged working ranges 702, 704 (or working planes), whereby the upper working range 702 allows working in automatic positioning mode (View A) and the lower working range 704 allows working in manual positioning mode (View B).

In automatic positioning mode the linear drive module 108 moves the 3D measurement camera 102 and thus the measurement volume 144 with the aid of an autofocus controller before every recording and without any manual interaction parallel to the optical axis of the camera into the area of the dental shaped part which is to be recorded.

Here in automatic positioning mode the 3D measurement camera is located in the upper working range 702. In the representation in View A the robot arm 706 with its positioning means is for example in the neutral position for the 'overview recording' mode.

To implement manual positioning mode (View B) the extraoral dental scanner 100 has in addition a work plate 708 for manual positioning of a dental shaped part 300. The work plate 708, viewed from the 3D measurement camera 102 in the direction of its optical axis 106, is here arranged in such a way behind the model rotation module 126 that this and the work plate 708 cannot collide. The work plate 708 here lies in a plane perpendicular to the optical axis 106. The robot arm 706 is here in a 'parking position' (View B) in manual positioning mode.

In the case of the parking position shown in FIG. 7B the second tilting module 114 is set to +60°, the third swiveling module 118 is set to −105° and the fourth model-height compensation elevation module 122 is moved fully downwards to −25 mm.

In manual positioning mode different designs of dental shaped parts 300, including those using articulators, arranged on the work plate can be captured three-dimensionally (in FIG. 7, View B shown as an example). In manual positioning of the dental shaped part 300 there is first a rough positioning of the 3D measurement camera by means of at least one photoelectric beam, while fine positioning is carried out by an autofocusing device.

By articulator is meant a device for simulating the movement of the mandibular joint. To do so plaster models of the dental arches of the upper and lower jaws are mounted in the articulator. The movement of the jaws relative to each other can then be simulated.

An image field within the meaning of the description of the invention is a section through the measurement volume in the focal plane, where the sectional plane stands perpendicular to the optical axis.

A buccal recording is a recording on the cheek side, and a lingual recording is a recording on the tongue side.

A unilateral and rotatably fixed object, in other words, for example, an axis, a shaft, a cardan axis, a cardan shaft or similar is rotatably fixed or supported only at one of its two ends and is only there powered or rotated. The other end is not fixed on or to a further object or has no support.

A 3D measurement camera is for example an optical camera for capturing the three-dimensional surface structure of an object by means of, for example, a structured-light projector.

Positioning means within the meaning of the description of the invention are means for the relative positioning of the 3D measurement camera and of the dental shaped part.

Robot arm 706 within the meaning of the description of the invention refers to the unit consisting of tilting module 114, swiveling module 118, model-height compensation elevation module 122, model rotation module 126 and model plate 130.

REFERENCE NUMBERS 100 extraoral dental scanner
102 3D measurement camera
104 measurement volume
106 optical axis
108 camera elevation module (linear drive module)
110 travel range of the linear axis of the camera elevation module
112 first axis/linear axis of the camera elevation module
114 tilting module 114
116 second axis/axis of rotation of the tilting module
118 swiveling module
120 third axis/axis of rotation of the swiveling module
122 model-height compensation elevation module
124 fourth axis/linear axis of the model-height compensation elevation module
126 model rotation module
128 fifth axis/axis of rotation of the model rotation module
130 model plate
132 immovable assembly of the dental scanner
134 angular range of the axis of rotation of the tilting module
136 angular range of the axis of rotation of the swiveling module
137 travel range of the linear axis of the model-height compensation elevation module
138 direction of movement (direction of rotation) of the model plate
140 center of the model plate
142 center of the measurement volume (intersection of the axis of rotation of the tilting module, axis of rotation of the swiveling module and linear axis of the camera elevation module)
144 measurement volume
146 offset (distance) between the model rotation axis and the intersection of the axis of rotation of the swiveling module with the axis of rotation of the tilting module (center of the cardan joint in the neutral position)
200 image field
202 image field diagonal 204 image field center
300 dental shaped part
700 housing
702 upper working range
704 lower working range
706 robot arm (consisting of tilting module 114, swiveling module 118, model-height compensation elevation module 122, model rotation module 126, and model plate 130)
708 work plate

The invention claimed is:

1. An extraoral dental scanner for three-dimensional capture of a surface of a dental shaped part, comprising:
a three-dimensional measurement camera for three-dimensional capture of a surface of a dental shaped part in a measurement volume of the three-dimensional measurement camera; and
a 5-axis relative positioning system configured to relatively position the three-dimensional measurement camera and the dental shaped part, wherein the 5-axis relative positioning system includes:
(i) a camera elevation module for moving the three-dimensional measurement camera along a camera elevation module linear axis,
(ii) a holding unit including a model rotation module, the holding unit configured to hold the dental shaped part, with the holding unit being rotatable about a holding unit rotational axis,
(iii) a tilting module that is rotatable about a tilting module rotational axis,
(iv) a swiveling module attached to the tilting module, the swiveling module being rotatable about a swiveling module rotational axis, and
(v) a model-height compensation module attached to the swiveling module and movable along a model-height compensation elevation module linear axis,
wherein the swiveling module rotational axis, the tilting module rotational axis, and the holding unit rotational axis, are all substantially perpendicular to each other, and
wherein the holding unit is connected to the swiveling module so as to be rotatable about the swiveling module rotational axis.

2. The extraoral dental scanner according to claim 1, wherein
the model rotation module of the holding unit is attached to the model-height compensation elevation module and is rotatable about a model rotation module rotational axis that runs substantially parallel to the model-height compensation elevation module linear axis, and
wherein the holding unit further includes a model plate that is rotatably supported on the model rotation module, a center of the model plate is on the model rotation module rotational axis, and
wherein the camera elevation module linear axis, the tilting module rotational axis, and the swiveling module rotational axis are all substantially perpendicular to each other and coincident with each other at a center of the measurement volume.

3. The extraoral dental scanner according to claim 2, wherein the model rotation module rotational axis is at a separation distance from the camera elevation module linear axis when the tilting module and the swiveling module are rotated to respective positions such that the model rotation module rotational axis is aligned parallel to the camera elevation module linear axis.

4. The extraoral dental scanner according to claim 3, wherein the separation distance is at least 22 mm but no more than 26 mm.

5. The extraoral dental scanner according to claim 2, wherein the camera elevation module has a travel range of +25 mm to −170 mm along the camera elevation module linear axis,
wherein the tilting module has an angular range about the tilting module rotational axis of +60° to −60°,
wherein the swiveling module has an angular range about the tilting module rotational axis of +60° to −105°,
wherein the model-height compensation module has a travel range of +25 mm to −25 mm along the model-height compensation module linear axis, and
wherein the model rotation module has an angular range about the model rotational module rotational axis of 0-360°.

6. The extraoral dental scanner according to claim 2, wherein the model plate is circular and a diagonal of a measurement field of the three-dimensional measurement camera is at least as long as a radius of the model plate.

7. The extraoral dental scanner according to claim 2, wherein the camera elevation module is connected to an image processing device for automatic focusing of the three-dimensional measurement camera.

8. The extraoral dental scanner according to claim 1, wherein the three-dimensional measurement camera includes an optical image-recording camera and a structured-light projector, and wherein the three-dimensional measurement camera is configured to capture the surface of the dental shaped part using planar triangulation.

9. The extraoral dental scanner according to claim 1, wherein the 5-axis relative positioning system is configured to move the holding unit into a parking position outside a region which can be optically captured by the three-dimensional measurement camera.

10. The extraoral dental scanner according to claim 9,
wherein a work plate is for manually positioning the dental shaped part within the measurement volume of the three-dimensional measurement camera,
wherein the work plate is aligned substantially perpendicularly to an optical axis of the three-dimensional measurement camera, and
wherein the work plate is behind the holding unit when viewed from the three-dimensional measurement camera.

11. The extraoral dental scanner according to claim 10, further comprising: a photoelectric beam generator configured to generate at least one photoelectric beam for a rough positioning of the three-dimensional measurement camera during a manual positioning of the dental shaped part.

12. An extraoral dental scanner for three-dimensional capture of a surface of a dental shaped part, comprising:
a three-dimensional measurement camera for three-dimensional capture of a surface of a dental shaped part in a measurement volume of the three-dimensional measurement camera; and
a relative positioning system configured to relatively position the three-dimensional measurement camera and the dental shaped part, wherein the relative positioning system includes:
(i) a holding unit configured to hold the dental shaped part, with the holding unit being rotatable about a holding unit rotational axis,
(ii) a tilting module that is rotatable about a tilting module rotational axis, and (iii) a swiveling module attached to the tilting module, the swiveling module being rotatable about a swiveling module rotational axis, wherein the swiveling module rotational axis, the tilting module rotational axis, and the holding unit rotational axis, are all substantially perpendicular to each other, wherein the holding unit is connected to the swiveling module so as to be rotatable about the swiveling module rotational axis, and wherein the relative positioning system is configured to move the holding unit into a parking position outside a region which can be optically captured by the three-dimensional measurement camera.

13. An extraoral dental scanner for the three-dimensional capture of a surface of a dental shaped part comprising:

a 3D measuring camera for the three-dimensional capture of the surface of the dental shaped part in a measurement volume of the 3D measurement camera, the 3D measurement camera having an optical axis;

a relative positioning system configured to relatively position the three-dimensional measurement camera and the dental shaped part, wherein the relative positioning system includes:

(i) a holding unit configured to hold the dental shaped part, with the holding unit being rotatable about a holding unit rotational axis, (ii) a tilting module that is rotatable about a tilting module rotational axis, and (iii) a swiveling module attached to the tilting module, the swiveling module being rotatable about a swiveling module rotational axis, a work plate for manual positioning of the dental shaped part within the measurement volume of the 3D measurement camera, the work plate is aligned perpendicularly to the optical axis, wherein the work plate as seen from the 3D measurement camera is disposed behind the holding unit, wherein the swiveling module rotational axis, the tilting module rotational axis, and the holding unit rotational axis, are all substantially perpendicular to each other, wherein the relative positioning system is further configured to move the holding unit into a parking position outside a region which can be optically captured by the three-dimensional measurement camera;

the extraoral dental scanner further comprising a first work area configured to automatically position the dental shaped part and a second work area configured to manually position the dental shaped part, wherein the work plate is disposed in the second work area and, wherein the first and the second work areas are disposed along said optical axis.

* * * * *